(12) United States Patent
Uthe et al.

(10) Patent No.: US 9,994,506 B2
(45) Date of Patent: Jun. 12, 2018

(54) PROCESS FOR TRANSITIONING REACTORS FROM BASE-CATALYZED POLYOL PRODUCTION TO DMC-CATALYZED POLYOL PRODUCTION

(71) Applicant: Covestro LLC, Pittsburgh, PA (US)

(72) Inventors: Peter Uthe, Hickory, NC (US); Jack R. Reese, Coraopolis, PA (US); Stephen Bailey, Nitro, WV (US)

(73) Assignee: COVESTRO LLC, Pittsburgh, PA (US)

( * ) Notice: Subject to any disclaimer, the term of this patent is extended or adjusted under 35 U.S.C. 154(b) by 0 days. days.

(21) Appl. No.: 15/133,819

(22) Filed: Apr. 20, 2016

(65) Prior Publication Data

US 2017/0305826 A1    Oct. 26, 2017

(51) Int. Cl.
  *C07C 41/26*    (2006.01)
  *C08G 65/26*    (2006.01)

(52) U.S. Cl.
  CPC .......... *C07C 41/26* (2013.01); *C08G 65/2663* (2013.01); *C08G 65/2669* (2013.01)

(58) Field of Classification Search
  CPC .................................................... C07C 41/46
  See application file for complete search history.

(56) References Cited

U.S. PATENT DOCUMENTS

| | | |
|---|---|---|
| 3,427,256 A | 2/1969 | Milgrom |
| 3,427,334 A | 2/1969 | Belner |
| 3,427,335 A | 2/1969 | Herold |
| 3,829,505 A | 8/1974 | Herold |
| 4,472,560 A | 9/1984 | Kuyper et al. |
| 4,477,589 A | 10/1984 | van der Hulst et al. |
| 5,158,922 A | 10/1992 | Hinney et al. |
| 5,470,813 A | 11/1995 | Le-Khac |
| 5,482,908 A | 1/1996 | Le-Khac |
| 5,545,601 A | 8/1996 | Le-Khac |
| 5,689,012 A | 11/1997 | Pazos et al. |
| 6,689,710 B2 | 2/2004 | Grosch et al. |
| 6,764,978 B2 | 7/2004 | Grosch et al. |
| 7,005,552 B2 | 2/2006 | Kaushiva |
| 7,553,921 B2 | 6/2009 | Suzuki et al. |
| 7,919,575 B2 | 4/2011 | Browne et al. |
| 8,530,602 B2 | 9/2013 | Suzuki et al. |
| 2005/0096488 A1 | 5/2005 | Kaushiva |
| 2010/0234647 A1 | 9/2010 | Browne |
| 2013/0338331 A1 | 12/2013 | Lorenz et al. |
| 2013/0345476 A1* | 12/2013 | Reese ..................... C07C 41/03 568/620 |

FOREIGN PATENT DOCUMENTS

| | | |
|---|---|---|
| EP | 1577334 A1 | 9/2005 |
| JP | 05331276 A | 12/1993 |

* cited by examiner

*Primary Examiner* — Rosalynd A Keys
(74) *Attorney, Agent, or Firm* — N. Denise Brown

(57) ABSTRACT

A process for transitioning a reactor from base-catalyzed polyol production to double metal cyanide (DMC)-catalyzed polyol production is described. The process includes discharging a base-catalyzed and un-neutralized product mixture from a reactor, and adding an acidified polyether polyol starter and DMC catalyst mixture to the reactor. A DMC-catalyzed polyol production reaction can then be conducted in the reactor without intermediate washing or rinsing of the reactor, and without catalyst deactivation from base or alkaline hold-up.

20 Claims, No Drawings

PROCESS FOR TRANSITIONING REACTORS FROM BASE-CATALYZED POLYOL PRODUCTION TO DMC-CATALYZED POLYOL PRODUCTION

BACKGROUND

Polyether polyols are used in the polyurethane industry for the production of polyurethane products such as coatings, sealants, adhesives, elastomers, and foams. The industrial production of polyether polyols generally involves two alternative reactions—either the base-catalyzed oxyalkylation of starter molecules or the double metal cyanide (DMC)-catalyzed oxyalkylation of starter molecules. The base and DMC catalysts used for the production of polyether polyols are incompatible because base catalysts deactivate DMC catalysts. Therefore, base-catalyzed polyol production and DMC-catalyzed polyol production generally require separate and dedicated production reactors to avoid cross-contamination of base compounds in DMC-catalyzed reaction mixtures. This can increase the cost of polyether polyol production and result in reactor under-utilization. An alternative is washing the reactor with polyol, solvent, water and/or an acidic solution when switching between base-catalyzed and DMC-catalyzed technologies in the same reactor. This creates significant waste from the wash that must be properly treated and disposed of, which increases production costs. The reactor must also be thoroughly dried to remove any trace solvent and/or water remaining in the reactor as these trace contaminants can decrease the activity of the DMC-catalyzed reaction and contribute to undesirable volatile organic compounds (VOCs) in the polyether product. Therefore, an improved process for switching between the base-catalyzed reaction and the DMC-catalyzed reaction is necessary.

SUMMARY

This specification describes a process for transitioning a reactor from base-catalyzed polyol production to DMC-catalyzed polyol production. In one example, the process comprises conducting a base-catalyzed polyol production reaction in a reactor, thereby producing a base-catalyzed product mixture. The base-catalyzed product mixture is discharged from the reactor without being neutralized. A starter mixture is then added to the reactor. The reactor is not washed-out or rinsed between the discharging of the base-catalyzed product mixture and the addition of the starter mixture. The starter mixture is added in an amount that contacts at least 12.5% of the total internal surface area of the reactor. The starter mixture comprises a polyether polyol starter, a DMC catalyst, and 500-1200 ppm acid based on the total weight of the starter mixture. A DMC-catalyzed polyol production reaction is then conducted in the reactor.

It is understood that the inventions described in this specification are not necessarily limited to the examples summarized in this Summary.

DESCRIPTION

The process described in this specification eliminates the need for separate production reactors dedicated to either base-catalyzed polyol production or DMC-catalyzed polyol production. The process facilitates the direct transition of a single reactor between the two reaction modes, without any intermediate washing of the reactor, cleaning of the reactor, rinsing of the reactor, or otherwise processing the reactor to remove residual base-catalyzed product after the un-neutralized product is discharged from the reactor, and without deactivation of the DMC catalyst from base or alkaline hold-up in the residual base-catalyzed product.

After the completion of a base-catalyzed polyol production reaction, the base-catalyzed product mixture contains residual amounts of the base catalyst. For example, the base-catalyzed product mixture may contain from 0.1% to 0.8% by weight of potassium hydroxide, sodium hydroxide, or cesium hydroxide. When the un-neutralized base-catalyzed product mixture is discharged from the reactor, a substantial amount of the base-catalyzed product mixture adheres to the internal surfaces of the reactor (e.g., internal walls, baffles, heat exchanger coils, dip tubes, sparge rings, agitator shafts, blades, impellers, spray nozzles, and the like) and remains in the reactor. The base compounds used to catalyze polyether polyol polymerization reactions (e.g., potassium hydroxide) strongly deactivate the DMC compounds; therefore, it is generally necessary to thoroughly wash/clean and rinse the inside of a base-catalyzed polymerization reactor before conducting a subsequent DMC-catalyzed polymerization reaction in the reactor. This need to thoroughly wash/clean, rinse, and dry the inside surfaces of the reactor to remove any residual base-catalyzed polyol product makes base-to-DMC-catalysis reactor transitions costly in terms of reactor downtime and increased maintenance. An alternative approach is to neutralize the base-catalyzed polyol product (e.g., by adding acid to the product) before discharging the product from the reactor. However, pre-discharge neutralization also increases production costs and inefficiently uses reactor time. These costs have led to the use of separate and dedicated reactors for base- and DMC-catalyzed polyols, which results in reactor under-utilization and increased capital costs. The present process addresses these issues by providing for the direct transition of a single reactor between base-catalyzed and DMC-catalyzed reaction modes for the production of polyether polyols.

The processes comprises the addition of 500-1200 ppm of an acid to a DMC catalyst starter mixture, based on the total weight of the starter mixture, and adding the acidified starter mixture to the alkaline-contaminated reactor in an amount that contacts at least 12.5% of the total internal surface area of the reactor. The acid added to the catalyst starter mixture must contact residual base-catalyzed product mixture in the reactor in order to effectively neutralize the residual base compounds and prevent DMC catalyst deactivation. However, residual base-catalyzed product mixture often adheres to high surface area internal components in a reactor and external recirculation loop, if present, such as on baffles, heat exchanger coils, dip tubes, sparge rings, agitator shafts, blades, impellers, spray nozzles, piping, pump and heat exchanger tubes in an external recirculation loop, and the like. As a result, an amount of acidified starter mixture must be added to the reactor to ensure contact with the residual base-catalyzed product mixture adhered to high surface area components inside the reactor. For example, DMC catalyst starter mixture comprising 500-1200 ppm of an acid based on the total weight of the starter mixture is added to the reactor in an amount that contacts at least 12.5% of the total internal surface area of the reactor. When at least 12.5% of the total internal surface area of the reactor and external recirculation loop, if present, including the surfaces of internal components such as on baffles, heat exchanger coils, dip tubes, sparge rings, agitator shafts, blades, impellers, and the like, contacts the DMC catalyst starter mixture comprising 500-1200 ppm of an acid, a sufficient amount of the residual base-catalyzed product mixture will contact the acidified starter mixture to effectively neutralize the residual base and prevent the alkaline deactivation of the DMC catalyst. By adding the starter mixture acidified with 500-1200 ppm of an acid to a reactor in an amount that contacts at least 12.5% of the total internal surface area of the reactor, a sufficient amount of the acid remains active to neutralize any base contaminants as the reactor fills.

The DMC catalyst starter mixture generally comprises: (a) a polyether polyol starter; (b) a DMC catalyst; and (c) 500-1200 ppm acid based on the total weight of the starter mixture.

The polyether polyol starter may comprise polyoxypropylene polyols, polyoxyethylene polyols, polytetramethylene ether glycols, propoxylated glycerols, alkoxylated allylic alcohols, and combinations of any thereof. For example, polyether polyol starter may comprise a polyoxypropylene triol having a hydroxyl number in the range of 200-300 mg KOH/g. The polyether polyol starter may be prepared using conventional polyether polyol production processes known in the art.

DMC catalysts suitable for use in the present process are described in U.S. Pat. Nos. 3,427,256; 3,427,334; 3,427,335; 3,829,505; 4,472,560; 4,477,589; 5,158,922; 5,470,813; 5,482,908; 5,545,601, 6,689,710; and 6,764,978, which are incorporated by reference into this specification. For example, the DMC catalyst may comprise a zinc hexacyanocobaltate compound prepared, for example, as described in U.S. Pat. No. 5,482,908. The DMC catalyst may be present in the starter mixture in an amount comprising 30-100 ppm of the total weight of the final product, or any sub-range subsumed therein, such as, for example, 30-90 ppm or 60-90 ppm.

Acids suitable for use in the present process include mineral acids, organic carboxylic acids, phosphonic acids, and sulfonic acids. For example, phosphoric acid is a suitable mineral acid, including monosodium phosphate and monopotassium phosphate salts of phosphoric acid, whereas acetic acid is a suitable organic acids. Acid derivatives which are reactive with bases, such as acid chlorides, acid anhydrides, and the like, also may be suitable. Examples of mineral acids which may be suitable also include hydrochloric acid, hydrobromic acid, and sulfuric acid, among others, while suitable carboxylic acids or their acidifying derivatives also may include formic acid, oxalic acid, citric acid, maleic acid, maleic anhydride, succinic acid, succinic anhydride, adipic acid, adipoyl chloride, adipic anhydride, and the like. As described above, the acid may be present in the starter mixture in an amount comprising 500-1200 ppm of the total weight of the starter mixture, or any sub-range subsumed therein, such as, for example, greater than 500 ppm to less than 1200 ppm, 500-1100 ppm, 500-1000 ppm, 500-900 ppm, 500-800 ppm, 500-700 ppm, 550-1200 ppm, 550-1100 ppm, 550-1000 ppm, 550-900 ppm, 550-800 ppm, 550-700 ppm 600-1200 ppm, 600-1100 ppm, 600-1000 ppm, 650-1000 ppm, 700-1000 ppm, 750-1000 ppm, or 800-1000 ppm.

In examples where the base-catalyzed product mixture from an immediately preceding base-catalyzed polyol production reaction comprises greater than 0.33% of residual base (e.g., potassium hydroxide) by weight of the base-catalyzed product mixture, the starter mixture may comprise less than 1200 ppm of the acid and at least Y ppm of the acid based on the total weight of the starter mixture, wherein:

$Y=810.0*X+232.4$; and wherein X is the weight percentage of residual base (e.g., potassium hydroxide) in the base-catalyzed product mixture. In examples where the base-catalyzed product mixture from an immediately preceding base-catalyzed polyol production reaction comprises greater than 0.33% of residual base (e.g., potassium hydroxide) by weight of the base-catalyzed product mixture, the starter mixture may comprises less than 1000 ppm of the acid and at least Y ppm of the acid based on the total weight of the starter mixture, wherein:

$Y=810.0*X+232.4$; and wherein X is the weight percentage of residual base (e.g., potassium hydroxide) in the base-catalyzed product mixture.

As described above, the starter mixture comprising the polyether polyol starter; the DMC catalyst; and the acid may be added to the reactor in an amount that contacts at least 12.5% of the total internal surface area of the reactor including an external recirculation loop, if present. The starter mixture may be added to the reactor in an amount that contacts at least 15%, at least 20%, at least 25%, at least 30%, at least 35%, at least 40%, at least 45%, or at least 50% of the total internal surface area of the reactor. The starter mixture may be added to the reactor in an amount that contacts 12.5-95%, 12.5-75%, 12.5-50%, 25-75%, or 25-50% of the total internal surface area of the reactor including an external recirculation loop, if present.

The starter mixture may be added to a reactor as a single charge or multiple charges. For example, the starter mixture may be added to the reactor as a first charge comprising approximately half of the polyether polyol starter and the acid, and a second charge comprising the balance of the polyether polyol starter and the DMC catalyst. Adding the starter mixture to the reactor as multiple charges can comprise the addition of two or more charges, wherein each charge comprises respective portions of the polyether polyol starter, the DMC catalyst, and the acid.

After the starter mixture is added to the reactor, the starter mixture may be heated in the reactor to a temperature in the range of 100-200° C. for 15-60 minutes before conducting the DMC-catalyzed polyol production reaction in the reactor. The starter mixture may be heated in the reactor to a temperature in the range of 100-200° C. or any sub-range subsumed therein, such as, for example, 130-150° C. The starter mixture may be heated in the reactor for a time in the range of 15-60 minutes or any sub-range subsumed therein, such as, for example, 15-30 minutes.

After the starter mixture is added to the reactor, and optionally heated as described above, a DMC-catalyzed polyol production reaction is conducted in the reactor. Conducting the DMC-catalyzed polyol production reaction may comprise heating the starter mixture in the reactor to a temperature in the range of 100-200° C. or any sub-range subsumed therein, such as, for example, 130-150° C. Conducting the DMC-catalyzed polyol production reaction may further comprise applying a vacuum and a nitrogen sparge to the reactor, sealing the reactor under vacuum, and activating the DMC catalyst by adding an initial charge of an alkylene oxide to the reactor. For example, an alkylene oxide such as propylene oxide, ethylene oxide, or combinations thereof, may be added to the reactor. The initial activating charge of the alkylene oxide may comprise 4-8% based on the total weight of the alkylene oxide and the starter mixture.

The activation time of the DMC catalyst (defined as the time required for the reactor pressure to drop by 50% of the maximum pressure reached during the addition of the initial activating charge of the alkylene oxide) may be less than 60 minutes, less than 45 minutes, less than 30 minutes, less than 25 minutes, less than 20 minutes, less than 15 minutes, or less than 10 minutes. Before the activation of the DMC catalyst with an initial charge of an alkylene oxide, the starter mixture may comprise zero alkalinity and an acid number of less than 0.20 mg KOH/g, less than 0.15 mg KOH/g, less than 0.10 mg KOH/g, or less than 0.05 mg KOH/g.

The DMC-catalyzed polyol production reaction may be conducted with a build ratio of less than 8. The build ratio of a polyol production reaction is the ratio of the number average molecular weight of the polyol product produced in the reaction to the number average molecular weight of the polyether polyol starter used in the reaction or the ratio of the final product weight to the starter weight. Higher build ratios correspond to lesser amounts of starter mixture in the reactor, and lower build ratios correspond to greater amounts of starter mixture in the reactor. Depending on the specific design of a reactor (and thus the specific internal surface area of the reactor and the surface area distribution among vessel walls and higher surface area components), the build ratio should be sufficiently low to ensure that the starter mixture contacts at least 12.5% of the internal surface area of reactor when added to the reactor and before catalyst activation. The DMC-catalyzed polyol production reaction may be conducted, for example, with a build ratio of less than 12, less than 10, less than 8, less than 7, less than 6, less than 5, or less than or equal to 4.

Conducting the DMC-catalyzed polyol production reaction may comprise conducting a semi-batch process, wherein an alkylene oxide (e.g., propylene oxide) is continuously added to the reactor during the DMC-catalyzed polyol production reaction. Conducting the DMC-catalyzed polyol production reaction may comprise conducting a continuous addition of starter (CAOS) process, wherein an alkylene oxide and additional starter are continuously added to the reactor during the DMC-catalyzed polyol production reaction.

EXAMPLES

Polyether Polyol Preparation

A base-catalyzed polyol production reaction and the resulting base-catalyzed product mixture were simulated by charging an 8 gallon continuously stirred tank reactor with 5 gallons of a mixture comprising a polyoxypropylene triol having a hydroxyl number of 56 mg KOH/g and 0.33% potassium hydroxide by total weight of the polyoxypropylene triol and potassium hydroxide ("base-catalyzed product simulant"). The base-catalyzed product simulant was stirred and heated in the reactor at a temperature of 100° C. for 60 minutes. The un-neutralized base-catalyzed product simulant was then discharged from the reactor with a nitrogen purge at 60° C. for 20 minutes.

A starter mixture was added to the discharged reactor in an amount sufficient to provide a build ratio of 8.5 (2414 grams). The reactor was not washed, rinsed, or otherwise processed to remove residual base-catalyzed product simulant after discharging from the reactor. The starter mixture comprised a polyether polyol starter (polyoxypropylene triol, hydroxyl number in the range of 233-243 mg KOH/g), 30-120 ppm of a zinc hexacyanocobaltate DMC catalyst based on the total weight of the final product, and 0 to 1000 ppm of phosphoric acid based on the total weight of the starter mixture. The starter mixture was heated in the reactor to 130° C. with a nitrogen purge under vacuum for 30 minutes. The reactor was then heated to a reaction temperature of 130-150° C., the reactor was sealed under the vacuum, and 4 to 10% propylene oxide was added to the sealed vacuum (by total weight of the starter mixture) to activate the DMC catalyst. If the catalyst did not initially activate a second charge of propylene oxide was added to assist in the catalyst—this activation amount, if used, did not exceed 12%.

The activation time of the DMC catalyst was measured as the time required for the reactor pressure to drop by 50% of the maximum pressure reached during the addition of the propylene oxide. The activation time is a measure of the activity of the catalyst—the shorter the activation time the more active the catalyst. After activation, the reactor was maintained at a reaction temperature of 130-150° C. and propylene oxide was added continuously over about 6.5 hours, after which the propylene oxide feed was discontinued (semi-batch operation, 18105 total grams of propylene oxide fed–activation+steady feed). The maximum pressure during the steady oxide feed was typically reached at the end of the oxide feed—this is documented as the peak pressure below. The peak pressure provides a measure of the activity of catalyst during the oxide feed—the higher the peak pressure the less active the catalyst. The reactor contents were maintained at a reaction temperature of 130-150° C. for 0.5 hours. Vacuum was then applied to the reactor to remove unreacted propylene oxide, and thereafter the DMC-catalyzed product was cooled and discharged from the reactor. The DMC-catalyzed product comprised a polyoxypropylene triol having a hydroxyl number of about 28 mg KOH/g. The following tables summarize the results.

TABLE 1

Comparative Examples at Acid Levels in Starter <500 ppm.

|  | Example | | | |
| --- | --- | --- | --- | --- |
|  | 1 | 2 | 3 | 4 |
| Catalyst Concentration (ppm) | 30 | 30 | 60 | 60 |
| Acid Added to Starter (ppm) | 0 | 25 | 125 | 125 |
| Activation Temperature (° C.) | 140 | 140 | 140 | 140 |
| Wt % PO for Activation (based on starter weight) | ⁴/₈* | ⁴/₈* | ⁴/₈* | 4 |
| Activation Time (min) | >150 | >150 | >150 | >150 |
| Peak Pressure (PSIA) | NR | NR | NR | NR |
| Hydroxyl Number (mgKOH/g) | ND | ND | ND | ND |
| Viscosity (cks @ 25° C.) | ND | ND | ND | ND |
| Molecular Weight Distribution (Mw/Mn) | ND | ND | ND | ND |

*4% activation charge was followed by second charge of 8%.

NR = No Reaction.

ND = No Data.

TABLE 2

Comparative Examples at Acid Levels in Starter <500 ppm.

| Example | 5 | 6 | 7 | 8 | 9 | 10 | 11 |
|---|---|---|---|---|---|---|---|
| Catalyst Concentration (ppm) | 30 | 30 | 30 | 60 | 60 | 60 | 60 |
| Acid Added to Starter (ppm) | 250 | 250 | 250 (95/5)** | 250 | 250 (75/25)** | 250 (50/50)** | 250 |
| Activation Temperature (° C.) | 140 | 130 | 140 | 140 | 140 | 140 | 140 |
| Wt % PO for Activation (based on starter weight) | 4 | 4 | 4 | 4/8* | 4 | 4/8* | 8 |
| Activation Time (min) | 5 | 14 | 10 | >150 | 50 | 66 | 6 |
| Peak Pressure (PSIA) | 51 | 72 | 52 | NR | 13.8 | 13.4 | 13.5 |
| Hydroxyl Number (mgKOH/g) | 27.7 | 27.9 | 27.8 | ND | 28 | 28 | 28.6 |
| Viscosity (cks @ 25° C.) | 2657 | 1695 | 2749 | ND | 1340 | 1334 | 1695 |
| Molecular Weight Distribution (Mw/Mn) | 1.372 | 1.123 | 1.335 | ND | 1.069 | 1.072 | 1.053 |

*4% activation charge was followed by second charge of 8%.
**95%, 75%, and 50% of starter, respectively, was added with acid and heated at 50° C. for 30 minutes and then the rest of the starter was added with catalyst.
NR = No Reaction.
ND = No Data.

TABLE 3

Comparative Examples at Acid Levels in Starter <500 ppm.

| | Example | | | | |
|---|---|---|---|---|---|
| | 12 | 13 | 14 | 15 | 16 |
| Catalyst Concentration (ppm) | 90 | 120 | 120 | 120 | 120 |
| Acid Added to Starter (ppm) | 250 | 250 | 250 | 250 | 250 |
| Activation Temperature (° C.) | 140 | 140 | 140 | 150 | 150 |
| Wt % PO for Activation (based on starter weight) | 4/8* | 4 | 4 | 10 | 10 |
| Activation Time (min) | >120 | 35 | 35 | 4 | 13 |
| Peak Pressure (PSIA) | NR | 13.6 | 13.2 | 11.8 | 22.4 |
| Hydroxyl Number (mgKOH/g) | ND | 28.1 | 28.1 | 28 | 28.3 |
| Viscosity (cks @ 25° C.) | ND | 1254 | 1248 | 1255 | 1375 |
| Molecular Weight Distribution (Mw/Mn) | ND | 1.057 | 1.047 | 1.059 | 1.145 |

*4% activation charge was followed by second charge of 8%.
NR = No Reaction.
ND = No Data.

TABLE 4

Inventive Examples at Acid Levels in Starter at 500 ppm.

| Example | 17 | 18 | 19 | 20 | 21 | 22 | 23 |
|---|---|---|---|---|---|---|---|
| Catalyst Concentration (ppm) | 30 | 30 | 60 | 60 | 60 | 60 | 90 |
| Acid Added to Starter (ppm) | 500 | 500 | 500 | 500 | 500 | 500 | 500 |
| Activation Temperature (° C.) | 140 | 140 | 150 | 140 | 140 | 150 | 140 |
| Wt % PO for Activation (based on starter weight) | 10 | 4 | 4 | 4 | 4 | 4 | 4 |
| Activation Time (min) | 12 | 10 | 11 | 8 | 130 | 125 | 13 |
| Peak Pressure (PSIA) | 13.3 | 23 | 12.6 | 29.5 | 12.7 | 22.6 | 34.9 |
| Hydroxyl Number (mgKOH/g) | 28 | 28.1 | 28.1 | 28.7 | 28.2 | 28.9 | 28.2 |

TABLE 4-continued

Inventive Examples at Acid Levels in Starter at 500 ppm.

| Example | 17 | 18 | 19 | 20 | 21 | 22 | 23 |
|---|---|---|---|---|---|---|---|
| Viscosity (cks @ 25° C.) | 1446 | 1716 | 1275 | 1266 | 1362 | 1369 | 1482 |
| Molecular Weight Distribution (Mw/Mn) | 1.117 | 1.196 | 1.059 | 1.061 | 1.116 | 1.152 | 1.102 |

TABLE 5

Inventive Examples at Acid Levels in Starter at ≥500 ppm.

| Example | 24 | 25 | 26 | 27 | 28 | 29 | 30 |
|---|---|---|---|---|---|---|---|
| Catalyst Concentration (ppm) | 90 | 120 | 45 | 60 | 90 | 120 | 120 |
| Acid Added to Starter (ppm) | 500 (95/5)** | 500 | 1000 | 1000 | 1000 | 1000 | 1000 |
| Activation Temperature (° C.) | 140 | 130 | 150 | 130 | 140 | 140 | 140 |
| Wt % PO for Activation (based on starter weight) | 4 | 8 | 8 | 10 | 4 | 4 | 8 |
| Activation Time (min) | 15 | 26 | 104 | 77 | 20 | 80 | 40 |
| Peak Pressure (PSIA) | 21.9 | 11.5 | 13.1 | 12.3 | 17.1 | 14.6 | 28 |
| Hydroxyl Number (mgKOH/g) | 27.8 | 28 | 28.6 | 28.1 | 27.8 | 28.2 | 28.2 |
| Viscosity (cks @ 25° C.) | 1577 | 1288 | 1484 | 1396 | 1415 | 1317 | 1323 |
| Molecular Weight Distribution (Mw/Mn) | 1.134 | 1.054 | 1.194 | 1.097 | 1.10 | 1.062 | 1.114 |

**95% of starter added with acid and heated at 50° C. for 30 minutes and then the rest of the starter was added with catalyst.

The addition of the acid to the starter mixture for the DMC-catalyzed polyol production reaction effectively neutralized the residual base-catalyzed product simulant remaining in the reactor, as evidenced by the activation of the DMC catalyst and the production of the DMC-catalyzed polyoxypropylene triol product. Catalyst and acid levels affect the activation times, peak pressure and product quality as measured by viscosity and molecular weight distribution (higher viscosity and/or molecular weight distribution indicates lower catalyst activity).

Example 31

Example 23 (90 ppm catalyst, 500 ppm phosphoric acid, 140° C. reaction temperature, 4% PO added for activation) was repeated, except, instead of adding the starter mixture to the reactor without washing, cleaning, rinsing, or otherwise processing the reactor to remove residual base-catalyzed product simulant after discharging from the reactor, 0.9% of the base-catalyzed product simulant was added to the starter mixture (by total weight of the starter mixture and the added based-catalyzed product simulant, 177 grams). The starter mixture comprising the 0.9% of the base-catalyzed product simulant was added to a clean reactor with no residual base-catalyzed product simulant from a prior base-catalyzed polyol production simulation. The activation time of the DMC catalyst was 5 minutes and the reactor maintained typical pressure for DMC-catalyzed polymerization with a peak pressure of 13.9 psia. The final product had a hydroxyl number of 27.9 mgKOH/g and a viscosity of 1379 cst at 25° C. and a molecular weight distribution Mw/Mn of 1.092.

This result indicated that the location of the residual base-catalyzed product simulant in the reactor (i.e., on internal walls, baffles, heat exchanger coils, dip tubes, sparge rings, agitator shafts, blades, impellers, and the like), as opposed to the amount of the residual base-catalyzed product simulant in the reactor, affects variation in catalyst activity throughout the batch.

Examples 32-34

Using a similar "base-catalyzed product simulant" to that above, a starter mixture was added to the discharged reactor in an amount sufficient to provide a build ratio of 4 (4968 grams). The reactor was not washed, rinsed, or otherwise processed to remove residual base-catalyzed product simulant after discharging from the reactor. The starter mixture comprised a polyether polyol starter (polyoxypropylene triol, hydroxyl number in the range of 233-243 mg KOH/g), 30-120 ppm of a zinc hexacyanocobaltate DMC catalyst based on the total weight of the final product, and 0 to 1000 ppm of phosphoric acid based on the total weight of the starter mixture. The starter mixture was heated in the reactor to 130° C. with a nitrogen purge under vacuum for 30 minutes. The reactor was then heated to reaction temperature 130-150° C., the reactor was sealed under the vacuum, and 4 to 10% propylene oxide was added to the sealed vacuum (by total weight of the starter mixture) to activate the DMC catalyst. If the catalyst did not initially activate a second charge of propylene oxide was added to assist in the catalyst—this activation amount did not exceed 12%.

The activation time of the DMC catalyst was measured as the time required for the reactor pressure to drop by 50% of the maximum pressure reached during the addition of the propylene oxide. The activation time is a measure of the activity of the catalyst—the shorter the activation time the more active the catalyst or the better that the base was neutralized. After activation, the reactor was maintained at reaction temperature 130-150° C. and propylene oxide was added continuously over about 6 hours, after which the propylene oxide feed was discontinued (semi-batch operation, 15551 total grams of propylene oxide fed–activation+ steady feed). The maximum pressure during the steady oxide feed was typically reached at the end of the oxide feed—this is documented as the peak pressure below. The peak pressure provides a measure of the activity of catalyst during the oxide feed—the higher the peak pressure the less active the catalyst. The reactor contents were maintained at reaction temperature 130-150° C. for 0.5 hours. Vacuum was then applied to the reactor to remove unreacted propylene oxide, and thereafter the DMC-catalyzed product was cooled and discharged from the reactor. The DMC-catalyzed product comprised a polyoxypropylene triol having a hydroxyl number of about 57.5 mg KOH/g. The following table summarizes the results.

TABLE 6

Examples at Build Ratio of 4 or 25% Starter in Reactor.

| | Example | | |
|---|---|---|---|
| | 32 | 33 | 34 |
| Catalyst Concentration (ppm) | 90 | 90 | 90 |
| Acid Added to Starter (ppm) | 500 | 1172 | 2410 |
| Activation Temperature (° C.) | 140 | 140 | 140 |
| Wt % PO for Activation (based on starter weight) | 4 | 4 | 4 |
| Activation Time (min) | 11 | 42 | NR |
| Peak Pressure (PSIA) | 11.9 | 18.5 | NR |
| Hydroxyl Number (mgKOH/g) | 56.9 | 53.3 | ND |
| Viscosity (cks @ 25° C.) | 538 | 600 | ND |
| Molecular Weight Distribution (Mw/Mn) | 1.021 | 1.024 | ND |

NR = No reaction.
ND = No data.

The addition of the acid to the starter mixture for the DMC-catalyzed polyol production reaction effectively neutralized the residual base-catalyzed product simulant remaining in the reactor, as evidenced by the activation of the DMC catalyst and the production of the DMC-catalyzed polyoxypropylene triol product. The decrease of the build ratio from 8 (Examples 1-31) to 4 increased the internal surface area of the reactor contacted by the starter mixture from 12.5% to 25% of the total internal surface area of the reactor. Without intending to be bound by any theory, it is believed that the increased contact between the starter mixture and the internal surface area of the reactor resulted in an increase in contact between the neutralizing acid and the residual base-catalyzed product simulant, which more efficiently and effectively decreased the alkalinity and thus decreased the variability in the catalyst activation times.

Examples 32-34 indicated that increasing acid concentration correlates with increasing catalyst activation time and that acid concentrations greater than about 1200 ppm can prevent DMC catalysts from activating. The DMC catalyst activated in examples 32 and 33 and the reaction proceeded to completion, producing a DMC-catalyzed polyoxypropylene triol product having a hydroxyl number of about 56 mg KOH/g.

Examples 35-38

Examples 35-38 are similar to Examples 32-34 above with the exception that one liter of crude alkaline polyol containing 0.33% KOH, neutralized with phosphoric acid was added to the starter mixture (~3000 ppm phosphoric acid added to crude alkaline polyol for neutralization). The reactor was also subjected to the "based-catalyzed product simulant" before the starter mixture was added.

TABLE 7

Examples at Build Ratio of 4 with 1 L of Neutralized Polyol Added to Starter Mixture.

| | Example | | | |
|---|---|---|---|---|
| | 35 | 36 | 37 | 38 |
| Catalyst Concentration (ppm) | 90 | 90 | 90 | 90 |
| Acid Added to Starter (ppm) | 0 | 500 | 500 | 750 |
| Activation Temperature (° C.) | 140 | 140 | 140 | 140 |
| Wt % PO for Activation (based on starter weight) | 4 | 4 | 4 | 4 |
| Activation Time (min) | 15 | 14 | 19 | 16 |
| Peak Pressure (PSIA) | 65* | 14.5 | 18.8 | 14.6 |
| Hydroxyl Number (mgKOH/g) | ND | 52.8 | 52.9 | 57.3 |
| Viscosity (cks @ 25° C.) | ND | 604 | 632 | 723 |
| Molecular Weight Distribution (Mw/Mn) | ND | 1.024 | 1.053 | 1.039 |

*Rapid pressure increase after restarting PO feed, run terminated due to high pressure.

Examples 35-38 were designed to stress the reactor transition by simulating a large amount of residual base-catalyzed product mixture. Example 35 did not include any acid added to the starter mixture (only the acid added to the 1 L of residual base-catalyzed product simulant). While the catalyst quickly activated, the run deactivated before completion, likely due to the residual potassium hydroxide from the drained simulant that was not neutralized by the acid added to the additional 1 L of residual base-catalyzed product simulant. This further indicates that catalyst activation is independent of the amount of residual base-catalyzed product simulant/mixture provided that the residual base is neutralized. Examples 36-38 included additional acid added to the starter mixture and these runs had fast catalyst activation and proceeded to completion, producing a DMC-catalyzed polyoxypropylene triol product having normal product properties.

Examples 39-41

In order to evaluate scalability, a series of DMC-catalyzed polyol production reactions were performed using the materials and procedures described above in connection with Examples 32-33, and with the parameters shown in Table 8. Examples 39-41 used an amount of starter mixture sufficient to provide a build ratio of 4 in an 80 gallon continuously stirred tank reactor (semi-batch operation). The reactor was not washed, rinsed, or otherwise processed to remove residual base-catalyzed product simulant after discharging from the reactor. In all cases the product simulant was a 60 OH# glycerin based all-PO polyol containing 0.34% KOH. Approximately 200 kg of this KOH containing material was circulated in the reactor at 105° C. for 1 hour. The scale-up reactor is equipped with a recirculation loop that includes a pump and heat exchanger. The un-neutralized base-catalyzed product simulant was circulated through the recirculation loop and external heat exchanger. The product simulant was discharged from the reactor after the hour mixing and recirculation time—no further cleaning or rinsing or neutralizing was done prior to charging the starter mixture.

The starter mixture was heated in the reactor to 130° C. with a nitrogen purge under vacuum for 30 minutes. The reactor was then heated to a reaction temperature of 130-150° C., the reactor was sealed under the vacuum, and 4 to 10% propylene oxide was added to the sealed vacuum (by total weight of the starter mixture) to activate the DMC catalyst. If the catalyst did not initially activate a second charge of propylene oxide was added to assist in the catalyst—this activation amount did not exceed 12%.

The activation time of the DMC catalyst was measured as the time required for the reactor pressure to drop by 50% of the maximum pressure reached during the addition of the propylene oxide. After activation, the reactor was maintained at a reaction temperature of 130-150° C. and propylene oxide was added continuously over about 6 hours, after which the propylene oxide feed was discontinued (semi-batch operation). The maximum pressure during the steady oxide feed was typically reached at the end of the oxide feed—this is documented as the peak pressure below. The reactor contents were maintained at the reaction temperature of 130-150° C. for 0.5 hours. Vacuum was then applied to the reactor to remove unreacted propylene oxide, and thereafter the DMC-catalyzed product was cooled and discharged from the reactor.

TABLE 8

Examples at Build Ratio of 4 in 80 gallon CSTR.

| | Example | | |
|---|---|---|---|
| | 39 | 40 | 41 |
| Catalyst Concentration (ppm) | 90 | 90 | 90 |
| Acid Added to Starter (ppm) | 500 | 500 | 500 |
| Activation Temperature (° C.) | 140 | 140 | 140 |
| Wt % PO for Activation (based on starter weight) | 4 | 4 | 8 |
| Activation Time (min) | 38 | 47 | 32 |
| Peak Pressure (PSIA) | 30 | 29 | 29 |
| Hydroxyl Number (mgKOH/g) | 56.2 | 56.6 | 56.5 |
| Viscosity (cks @ 25° C.) | 542 | 548 | 552 |
| Molecular Weight Distribution (Mw/Mn) | 1.07 | 1.029 | 1.028 |

Example 42

After the completion of Example 41, the DMC-catalyzed polyoxypropylene triol product was discharged from the reactor, and a starter mixture was added to the discharged reactor in an amount sufficient to provide a build ratio of 8. The reactor was not washed, rinsed, or otherwise processed to remove residual product from Example 41 after discharging from the reactor. The starter mixture comprised a polyether polyol starter (polyoxypropylene triol, hydroxyl number in the range of 233-243 mg KOH/g), 30 ppm of a zinc hexacyahocobaltate DMC catalyst based on the total weight of the final product, and no added acid. The reaction was conducted as described above in connection with Examples 39-41, and with the parameters shown in Table 9. The omission of the acid from the starter mixture for the DMC-catalyzed polyol production reaction, and the activation of the DMC catalyst and the production of the DMC-catalyzed polyoxypropylene triol product, demonstrates that only one DMC-catalyzed polyol production reaction using a starter mixture comprising acid is necessary to successfully transition a reactor from base-catalyzed polyol production to DMC-catalyzed polyol production.

TABLE 9

Examples at Build Ratio of 8 in 80 gallon CSTR with no acid after initial KOH-to-DMC transition.

| | Example 42 |
|---|---|
| Catalyst Concentration (ppm) | 30 |
| Acid Added to Starter (ppm) | 0 |
| Activation Temperature (° C.) | 130 |
| Wt % PO for Activation (based on starter weight) | 4 |
| Activation Time (min) | 32 |
| Peak Pressure (PSIA) | 35 |
| Hydroxyl Number (mgKOH/g) | 28 |
| Viscosity (cks @ 25° C.) | 1300 |
| Molecular Weight Distribution (Mw/Mn) | 1.08 |

Examples 43-54

A series of twelve polyol production reactions (Examples 43-54) were performed consecutively in an 8 gallon continuously stirred tank reactor. A based-catalyzed product simulant, as described above, was not used. Instead, Example 43 used a potassium hydroxide-catalyzed polyol production reaction. The product mixture of each example was discharged before the next example and the reactor was not washed, rinsed, neutralized or otherwise processed to remove residual product after discharging from the reactor. Examples 43-54 were performed with the parameters shown in Tables 10 and 11.

The base-catalyzed product mixture produced in Example 43 comprised 0.1% of potassium hydroxide by total weight of the base-catalyzed product mixture. The base-catalyzed product mixtures produced in Examples 46, 48, 50, and 52 comprised 0.7% of potassium hydroxide by total weight of the base-catalyzed product mixture. The base-catalyzed product mixtures were discharged from the reactor unneutralized.

The starter mixtures included the starter compounds in an amount sufficient to provide the build ratios listed in Tables 10 and 11. The polyether polyol starter in Examples 44, 45, 47, 49, 51, 53, and 54 was a polyoxypropylene triol having a hydroxyl number in the range of 233-243 mg KOH/g. The starter mixtures for the DMC-catalyzed runs included 90 ppm of a zinc hexacyanocobaltate DMC catalyst. The starter mixtures for the DMC-catalyzed runs also included phosphoric acid at the concentrations identified in Tables 10 and 11. The starter mixtures were added to the unwashed/unrinsed reactor. The reactor was heated to 130° C. with a nitrogen purge for 30 minutes in the DMC-catalyzed runs. The reactor was then heated to the activation temperatures listed in Tables 10 and 11, vacuum was applied to the reactor, and the reactor was sealed under the vacuum. The propylene oxide activator was added to the sealed reactor in the amount listed in Tables 10 and 11 to activate the DMC catalyst in the DMC-catalyzed runs.

TABLE 10

Consecutive Reactor Transitions Varying KOH content and acid content (Examples 43-48).

| Example | 43 | 44 | 45 | 46 | 47 | 48 |
|---|---|---|---|---|---|---|
| Reactor Condition | Clean | Ex. 43 drained | Ex. 43 product simulant | Ex. 44 | Ex. 46 | Ex. 47 |
| Starter | Glycerin | polyether polyol | polyether polyol | Glycerin | polyether polyol | Glycerin |
| Catalyst | KOH | DMC | DMC | KOH | DMC | KOH |
| Catalyst Concentration | 0.1% | 90 ppm | 90 ppm | 0.7% | 90 ppm | 0.7% |
| Acid Added to Starter (ppm) | 0 | 130 | 500 | 0 | 955 | 0 |
| Activation Temperature (° C.) | 115 | 140 | 140 | 115 | 140 | 115 |
| Wt % PO for Activation (based on starter weight) | NA | 4 | 4 | NA | 8 | NA |
| Activation Time (min) | NA | 2 | 5 | NA | 40 | NA |
| Build Ratio | 3.9 | 4 | 4 | 3.9 | 4 | 3.9 |
| Peak Pressure (PSIA) | 61 | 9 | 9 | 21 | 10 | 25 |
| Hydroxyl Number (mgKOH/g) | 458.0 | 59.8 | 58.4 | 446.0 | 60.5 | 470 |
| Viscosity (cks @ 25° C.) | ND | 525 | 558 | ND | 565 | ND |
| Molecular Weight Distribution (Mw/Mn) | ND | 1.013 | 1.098 | ND | 1.023 | ND |

NA = Not Applicable.
ND = No Data.

TABLE 11

Consecutive Reactor Transitions Varying KOH content and acid content (Examples 49-54).

| Example | 49 | 50 | 51 | 52 | 53 | 54 |
|---|---|---|---|---|---|---|
| Reactor Condition | Ex. 48 | Ex. 49 | Ex. 50 | Ex. 51 | Ex. 52 | Ex. 52 product simulant |
| Starter | polyether polyol | polyether polyol | polyether polyol | polyether polyol | polyether polyol | polyether polyol |
| Catalyst | DMC | KOH | DMC | KOH | DMC | DMC |

TABLE 11-continued

Consecutive Reactor Transitions Varying KOH content and acid content (Examples 49-54).

| Example | 49 | 50 | 51 | 52 | 53 | 54 |
|---|---|---|---|---|---|---|
| Catalyst Concentration | 90 ppm | 0.7% | 90 ppm | 0.7% | 90 ppm | 90 ppm |
| Acid Added to Starter (ppm) | 500 | 0 | 500 | 0 | 1000 | 800 |
| Activation Temperature (° C.) | 140 | 115 | 140 | 115 | 140 | 140 |
| Wt % PO for Activation (based on starter weight) | 8 | NA | 8 | NA | 4 | 4 |
| Activation Time (min) | 2 | NA | NR | NA | 24 | 6 |
| Build Ratio | 4 | 8 | 4 | 8 | 4 | 4 |
| Peak Pressure (PSIA) | 9 | 44 | 45 | 45 | 10 | 9 |
| Hydroxyl Number (mgKOH/g) | 60.1 | 38 | ND | 37.3 | 57.0 | 57.2 |
| Viscosity (cks @ 25° C.) | 518 | ND | ND | ND | 554 | 559 |
| Molecular Weight Distribution (Mw/Mn) | 1.015 | ND | ND | ND | 1.043 | 1.067 |

NA = Not Applicable
NR = No Reaction
ND = No Data

Other than Example 51, the addition of the acid to the starter mixture for the DMC-catalyzed polyol production reactions effectively neutralized the residual base-catalyzed product mixture remaining in the reactor, as evidenced by the activation of the DMC catalyst and the production of the DMC-catalyzed polyoxypropylene triol product. These runs further demonstrate that a DMC-catalyzed polyol production reaction using a starter mixture comprising acid can successfully transition a reactor from base-catalyzed polyol production to DMC-catalyzed polyol production, without any intermediate washing, cleaning, or rinsing of the reactor, and produce polyether polyols that meet product specifications.

Additionally, the runs in these examples facilitate the development of a predictive model for the minimum amount of acid to be added to a starter mixture to successfully transition a reactor from base-catalyzed polyol production to DMC-catalyzed polyol production. For example, when the preceding base-catalyzed product mixture comprises greater than 0.33% of residual base by weight of the base-catalyzed product mixture, the starter mixture can comprise at least Y ppm of acid based on the total weight of the starter mixture, wherein:

$Y = 810.0 * X + 232.4$; and wherein X is the weight percentage of residual base in the base-catalyzed product mixture.

Examples 55-73

While addition of acid to the starter mixture of a DMC-catalyzed polyol reaction facilitates the direct transition of the reactor from base-catalyzed polyol production to DMC-catalyzed polyol production, increasing acid concentration correlates with increasing catalyst activation time, and acid concentrations greater than about 1200 ppm can prevent DMC catalysts from activating. To further investigate this observation, a series of DMC-catalyzed polyol production reactions (Examples 55-73) were performed consecutively in a clean 1 liter continuously stirred tank reactor containing no residual base or base-catalyzed product mixture/simulant.

A starter mixture was added to the clean reactor in an amount sufficient to provide a build ratio of 4. The starter mixture comprised a polyether polyol starter (polyoxypropylene triol, hydroxyl number in the range of 233-243 mg KOH/g), 60 ppm of a zinc hexacyanocobaltate DMC catalyst based on the total weight of the final product, and varying amounts and types of acid, as shown in Tables 12-14.

The starter mixture was heated in the reactor to 130° C. with a nitrogen purge for 30 minutes. The reactor was then heated to 140° C., vacuum was applied to the reactor, the reactor was sealed under the vacuum, and 4% propylene oxide was added to the sealed vacuum (by total weight of the propylene oxide and the starter mixture) to activate the DMC catalyst.

The activation times of the DMC catalyst (measured as the time required for the reactor pressure to drop by 50% of the maximum pressure reached during the addition of the propylene oxide) are reported in Tables 12-14. After activation, the reactor was maintained at 140° C. for 0.5 hours. Vacuum was then applied to the reactor to remove unreacted propylene oxide, and thereafter the DMC-catalyzed activated starter mixture was cooled and discharged from the reactor. (An activation was only completed for these runs the reaction was not carried to completion)

TABLE 12

Effect of acid concentration of DMC catalyst activation (Examples 55-60).

| Example | 55 | 56 | 57 | 58 | 59 | 60 |
|---|---|---|---|---|---|---|
| Catalyst Concentration (ppm) | 60 | 60 | 60 | 60 | 60 | 60 |
| Acid | Phosphoric acid | Phosphoric acid | Phosphoric acid | Phosphoric acid | Phosphoric acid | Phosphoric acid |
| Acid Added to Starter (ppm) | 0 | 0 | 125 | 250 | 500 | 750 |
| Activation Temperature (° C.) | 140 | 140 | 140 | 140 | 140 | 140 |
| Wt % PO for Activation (based on starter weight) | 4 | 4 | 4 | 4 | 4 | 4 |
| Activation Time (min) | 7 | 9 | 12 | 15 | 18 | 48 |

TABLE 13

Effect of acid concentration of DMC catalyst activation (Examples 61-66).

| Example | 61 | 62 | 63 | 64 | 65 | 66 |
|---|---|---|---|---|---|---|
| Catalyst Concentration (ppm) | 60 | 60 | 60 | 60 | 60 | 60 |
| Acid | Phosphoric acid | Phosphoric acid | Phosphoric acid | Phosphoric acid | Phosphoric acid | Phosphoric acid |
| Acid Added to Starter (ppm) | 1000 | 1000 | 1250 | 1500 | 2000 | 3000 |
| Activation Temperature (° C.) | 140 | 140 | 140 | 140 | 140 | 140 |
| Wt % PO for Activation (based on starter weight) | 4 | 4 | 4 | 4 | 4 | 4 |
| Activation Time (min) | 25 | 30 | 134 | 83 | 170 | 117 |

TABLE 14

Effect of acid concentration of DMC catalyst activation (Examples 67-73).

| Example | 67 | 68 | 69 | 70 | 71 | 72 | 73 |
|---|---|---|---|---|---|---|---|
| Catalyst Concentration (ppm) | 60 | 60 | 60 | 60 | 60 | 60 | 60 |
| Acid | acetic acid | HCl | HCl | water | sodium monophosphate | sodium monophosphate | sodium monophosphate |
| Acid Added to Starter (ppm) | 1000 | 1000 | 372 | 180 | 1000 | 1000 | 5000 |
| Activation Temperature (° C.) | 140 | 140 | 140 | 140 | 140 | 140 | 140 |
| Wt % PO for Activation (based on starter weight) | 4 | 4 | 4 | 4 | 4 | 4 | 4 |
| Activation Time (min) | 14 | NR | 34 | 5 | 7 | 7 | 8 |

NR = No Reaction

As shown in Tables 12-14, increasing acid concentrations in the starter mixture correlates with increasing activation times (note that the absence of residual base eliminates alkaline deactivation of the DMC catalyst as a variable contributing to the increasing activation times). Acid concentrations above about 1200 ppm by total weight of the starter mixture substantially increase the catalyst activation time, but acid concentrations up to about 1200 ppm by total weight of the starter mixture do not substantially increase the catalyst activation time. Accordingly, a range of 500-

1200 ppm acid based on the total weight of the starter mixture may be effective to successfully transition a reactor from base-catalyzed polyol production to DMC-catalyzed polyol production.

Various aspect, features, and characteristics of the invention include, but are not limited to, the following numbered clauses.

1. A process for transitioning a reactor from base-catalyzed polyol production to double metal cyanide (DMC)-catalyzed polyol production, the process comprising:
   (i) conducting a base-catalyzed polyol production reaction in a reactor, thereby producing a base-catalyzed product mixture;
   (ii) discharging the base-catalyzed product mixture from the reactor, wherein the base-catalyzed product mixture is not neutralized before being discharged from the reactor;
   (iii) adding a starter mixture to the reactor, wherein the reactor is not washed-out or rinsed between the discharging of the base-catalyzed product mixture and the addition of the starter mixture, wherein the starter mixture is added in an amount that contacts at least 12.5% of the total internal surface area of the reactor, and wherein the starter mixture comprises:
      (a) a polyether polyol starter;
      (b) a DMC catalyst; and
      (c) 500-1200 ppm acid based on the total weight of the starter mixture; and
   (iv) conducting a DMC-catalyzed polyol production reaction in the reactor.
2. The process of clause 1, wherein the starter mixture is added in an amount that contacts at least 25% of the total internal surface area of the reactor.
3. The process of clause 1 or clause 2, wherein the DMC-catalyzed polyol production reaction is conducted with a build ratio of less than 8.
4. The process of any one of clauses 1-3, wherein the DMC-catalyzed polyol production reaction is conducted with a build ratio of less than 5.
5. The process of any one of clauses 1-4, wherein the starter mixture comprises 500-1000 ppm of the acid based on the total weight of the starter mixture.
6. The process of any one of clauses 1-5, wherein the base-catalyzed product mixture comprises greater than 0.33% of residual base by weight of the base-catalyzed product mixture, and wherein the starter mixture comprises less than 1200 ppm of the acid and at least Y ppm of the acid based on the total weight of the starter mixture, wherein:

$Y=810.0*X+232.4$; and wherein X is the weight percentage of residual base in the base-catalyzed product mixture.
7. The process of any one of clauses 1-6, wherein the base-catalyzed product mixture comprises greater than 0.33% of residual base by weight of the base-catalyzed product mixture, and wherein the starter mixture comprises a maximum of 1000 ppm of the acid and at least Y ppm of the acid, based on the total weight of the starter mixture, wherein:

$Y=810.0*X+232.4$; and wherein X is the weight percentage of residual base in the base-catalyzed product mixture.
8. The process of any one of clauses 1-7, wherein the starter mixture comprises zero alkalinity and an acid number of less than 0.20 mg KOH/g before activation of the DMC catalyst.
9. The process of any one of clauses 1-8, wherein the starter mixture comprises zero alkalinity and an acid number of less than 0.15 mg KOH/g before activation of the DMC catalyst.
10. The process of any one of clauses 1-9, wherein the starter mixture comprises 60-90 ppm of the DMC catalyst based on the total weight of the starter mixture.
11. The process of any one of clauses 1-10, further comprising heating the starter mixture in the reactor to a temperature in the range of 130-150° C. for 15-60 minutes before conducting the DMC-catalyzed polyol production reaction in the reactor.
12. The process of any one of clauses 1-11, wherein the base catalyst comprises potassium hydroxide.
13. The process of any one of clauses 1-12, wherein the polyether polyol starter comprises a polyoxypropylene triol having a hydroxyl number in the range of 200-300 mg KOH/g.
14. The process of any one of clauses 1-13, wherein the DMC catalyst comprises zinc hexacyanocobaltate.
15. The process of any one of clauses 1-14, wherein the acid comprises phosphoric acid.
16. The process of any one of clauses 1-15, wherein conducting the DMC-catalyzed polyol production reaction in the reactor comprises heating the starter mixture in the reactor to a temperature in the range of 130-150° C., applying a vacuum to the reactor, and activating the DMC catalyst by adding 4-8% of an alkylene oxide to the reactor based on the total weight of the alkylene oxide and the starter mixture.
17. The process of clause 16, wherein the alkylene oxide comprises propylene oxide.
18. The process of clause 16 or clause 17, wherein the activation time of the DMC catalyst is less than 30 minutes.
19. The process of any one of clauses 1-18, wherein conducting the DMC-catalyzed polyol production reaction in the reactor comprises conducting a semi-batch process, wherein an alkylene oxide is continuously added to the reactor during the DMC-catalyzed polyol production reaction.
20. The process of any one of clauses 1-19, wherein conducting the DMC-catalyzed polyol production reaction in the reactor comprises conducting a continuous addition of starter (CAOS) process, wherein an alkylene oxide and additional starter are continuously added to the reactor during the DMC-catalyzed polyol production reaction.
21. The process of any one of clauses 1-20, wherein the base-catalyzed product mixture contains from 0.1% to 0.8% by weight of potassium hydroxide, sodium hydroxide, or cesium hydroxide.

Various features and characteristics of the invention are described in this specification to provide an overall understanding of the disclosed processes and products. It is understood that the various features and characteristics described in this specification can be combined in any suitable manner regardless of whether such features and characteristics are expressly described or illustrated in combination in this specification. The Applicant expressly intends such combinations of features and characteristics to be included within the scope of this specification. As such, the claims can be amended to recite, in any combination, any features and characteristics expressly or inherently described in, or otherwise expressly or inherently supported by, this specification. Furthermore, the Applicant reserves the right to amend the claims to affirmatively disclaim features and characteristics that may be present in the prior art, even if those features and characteristics are not expressly described in this specification. Therefore, any such amendments will not add new matter to the specification or claims, and will comply with written description, sufficiency of description, and added matter requirements (e.g., 35 U.S.C. § 112(a) and Article 123(2) EPC). The compositions and products described in this specification can comprise, consist of, or consist essentially of the various features and characteristics described in this specification.

Also, any numerical range recited in this specification describes all sub-ranges of the same numerical precision (i.e., having the same number of specified digits) subsumed within the recited range. For example, a recited range of "1.0 to 10.0" describes all sub-ranges between (and including) the recited minimum value of 1.0 and the recited maximum value of 10.0, such as, for example, "2.4 to 7.6," even if the range of "2.4 to 7.6" is not expressly recited in the text of the specification. Accordingly, the Applicant reserves the right to amend this specification, including the claims, to expressly recite any sub-range of the same numerical precision subsumed within the ranges expressly recited in this specification. All such ranges are inherently described in this specification such that amending to expressly recite any such sub-ranges will not add new matter to the specification or claims, and will comply with written description, sufficiency of description, and added matter requirements (e.g., 35 U.S.C. § 112(a) and Article 123(2) EPC). Additionally, numerical parameters described in this specification should be construed in light of the number of reported significant digits, the numerical precision of the number, and by applying ordinary rounding techniques. It is also understood that numerical parameters described in this specification will necessarily possess the inherent variability characteristic of the underlying measurement techniques used to determine the numerical value of the parameter.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and can be employed or used in an implementation of the described compositions and products. Further, the use of a singular noun includes the plural, and the use of a plural noun includes the singular, unless the context of the usage requires otherwise.

Any patent, publication, or other disclosure material identified in this specification is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference. Any material, or portion thereof, that is incorporated by reference into this specification, but which conflicts with existing definitions, statements, or other disclosure material set forth herein, is only incorporated to the extent that no conflict arises between that incorporated material and the existing disclosure material. Applicant reserves the right to amend this specification to expressly recite any subject matter, or portion thereof, incorporated by reference.

What is claimed is:

1. A process for transitioning a reactor from base-catalyzed polyol production to double metal cyanide (DMC)-catalyzed polyol production, the process comprising:
    (i) conducting a base-catalyzed polyol production reaction in a reactor, thereby producing a base-catalyzed product mixture;
    (ii) discharging the base-catalyzed product mixture from the reactor, wherein the base-catalyzed product mixture is not neutralized before being discharged from the reactor:
    (iii) adding a starter mixture to the reactor, wherein the reactor is not washed-out or rinsed between the discharging of the base-catalyzed product mixture and the addition of the starter mixture, wherein the starter mixture is added in an amount that contacts at least 12.5% of the total internal surface area of the reactor, and wherein the starter mixture comprises.
        (a) a polyether polyol starter;
        (b) a DMC catalyst; and
        (c) 500-1200 ppm acid based on the total weight of the starter mixture; and
    (iv) conducting a DMC-catalyzed polyol production reaction in the reactor.

2. The process of claim 1, wherein the starter mixture is added in an amount that contacts at least 25% of the total internal surface area of the reactor.

3. The process of claim 1, wherein the DMC-catalyzed polyol production reaction is conducted with a build ratio of less than 8.

4. The process of claim 1, wherein the DMC-catalyzed polyol production reaction is conducted with a build ratio of less than 5.

5. The process of claim 1, wherein the starter mixture comprises 500-1000 ppm of the acid based on the total weight of the starter mixture.

6. The process of claim 1, wherein the base-catalyzed product mixture comprises greater than 0.33% of residual base by weight of the base-catalyzed product mixture, and wherein the starter mixture comprises less than 1200 ppm of the acid and at least Y ppm of the acid based on the total weight of the starter mixture. wherein:

$$Y=810.0*X+232.4; \text{ and}$$

wherein X is the weight percentage of residual base in the base-catalyzed product mixture.

7. The process of claim 1, wherein the base-catalyzed product mixture comprises greater than 0.33% of residual base by weight of the base-catalyzed product mixture, and wherein the starter mixture comprises a maximum of 1000 ppm of the acid and at least Y ppm of the acid, based on the total weight of the starter mixture, wherein:

$$Y=810.0*X+232.4; \text{ and}$$

wherein X is the weight percentage of residual base in the base-catalyzed product mixture.

8. The process of claim 1, wherein the starter mixture comprises zero alkalinity and an acid number of less than 0.20 mg KOH/g before activation of the DMC catalyst.

9. The process of claim 1, wherein the starter mixture comprises zero alkalinity and an acid number of less than 0.15 mg KOH/g before activation of the DMC catalyst.

10. The process of claim 1, wherein the starter mixture comprises 60-90 ppm of the DMC catalyst based on the total weight of the starter mixture.

11. The process of claim 1, further comprising heating the starter mixture in the reactor to a temperature in the range of 130-150° C. for 15-60 minutes before conducting the DMC-catalyzed polyol production reaction in the reactor.

12. The process of claim 1, wherein the base catalyst comprises potassium hydroxide.

13. The process of claim 1, wherein the polyether polyol starter comprises a polyoxypropylene triol having a hydroxyl number in the range of 200-300 mg KOH/g.

14. The process of claim 1, wherein the DMC catalyst comprises zinc hexacyanocobaltate.

15. The process of claim 1, wherein the acid comprises phosphoric acid.

16. The process of claim 1, wherein conducting the DMC-catalyzed polyol production reaction in the reactor comprises heating the starter mixture in the reactor to a temperature in the range of 130-150° C., applying a vacuum to the reactor, and activating the DMC catalyst by adding 4-8% of an alkylene oxide to the reactor based on the total weight of the alkylene oxide and the starter mixture.

17. The process of claim 16, wherein the alkylene oxide comprises propylene oxide.

18. The process of claim 1, wherein conducting the DMC-catalyzed polyol production reaction in the reactor comprises conducting a semi-batch process, wherein an alkylene oxide is continuously added to the reactor during the DMC-catalyzed polyol production reaction.

19. The process of claim 1, wherein conducting the DMC-catalyzed polyol production reaction in the reactor comprises conducting a continuous addition of starter (CAOS) process, wherein an alkylene oxide and additional starter are continuously added to the reactor during the DMC-catalyzed polyol production reaction.

20. The process of claim 1, wherein the base-catalyzed product mixture contains from 0.1% to 0.8% by weight of potassium hydroxide, sodium hydroxide, or cesium hydroxide.

* * * * *